United States Patent
Suresh et al.

(10) Patent No.: US 10,451,633 B2
(45) Date of Patent: Oct. 22, 2019

(54) ANTI-NUCLEAR ANTIBODY DETECTION AND DIAGNOSTICS FOR SYSTEMIC AND NON-SYSTEMIC AUTOIMMUNE DISORDERS

(71) Applicant: Immco Diagnostics, Inc., Buffalo, NY (US)

(72) Inventors: Lakshmanan Suresh, Williamsville, NY (US); Kishore Malyavantham, Williamsville, NY (US)

(73) Assignee: Immco Diagnostics, Inc., Buffalo, NY (US)

( * ) Notice: Subject to any disclaimer, the term of this patent is extended or adjusted under 35 U.S.C. 154(b) by 0 days.

(21) Appl. No.: 15/124,175

(22) PCT Filed: Mar. 24, 2015

(86) PCT No.: PCT/US2015/022120
§ 371 (c)(1),
(2) Date: Sep. 7, 2016

(87) PCT Pub. No.: WO2015/148431
PCT Pub. Date: Oct. 1, 2015

(65) Prior Publication Data
US 2017/0176454 A1  Jun. 22, 2017

Related U.S. Application Data

(60) Provisional application No. 61/969,771, filed on Mar. 24, 2014.

(51) Int. Cl.
*C12N 15/85* (2006.01)
*G01N 33/68* (2006.01)
*G01N 33/50* (2006.01)
*G01N 33/564* (2006.01)

(52) U.S. Cl.
CPC ......... *G01N 33/6854* (2013.01); *C12N 15/85* (2013.01); *G01N 33/5005* (2013.01); *G01N 33/564* (2013.01)

(58) Field of Classification Search
None
See application file for complete search history.

(56) References Cited

U.S. PATENT DOCUMENTS

| | | | |
|---|---|---|---|
| 5,518,881 A | 5/1996 | Gordon et al. | |
| 6,750,052 B1 | 6/2004 | Shinohara et al. | |
| 8,318,440 B2 | 11/2012 | Lea | |
| 2008/0206140 A1 | 8/2008 | Hickey et al. | |
| 2013/0310266 A1 | 11/2013 | Liang | |
| 2014/0068797 A1 | 3/2014 | Doudna et al. | |
| 2014/0370526 A1 | 12/2014 | Greenberg | |

FOREIGN PATENT DOCUMENTS

| | | |
|---|---|---|
| WO | 2008103265 A2 | 8/2008 |
| WO | 2013006156 A1 | 1/2013 |
| WO | 2013/083552 A1 | 6/2013 |

OTHER PUBLICATIONS

Akiyama et al (Nucleic Acid Research, 2000. vol. 28, No. 16, pp. i-vi).*
Chylack et al. Experimental Eye Research, 2004. vol. 79, pp. 941-948.*
Mariz et al (Arthritis & Rheumatism, 2011, vol. 63, No. 1, pp. 191-200).*
R. Badia et al.; "Zinc Finger Endonuclease Targeting PSIP1 Inhibits HIV-1 Integration"; Antimicrobial Agents and Chemotherapy; vol. 58, No. 8; May 12, 2014; pp. 4318-4327; XP055348697.
EP Patent Application No. 15768594.2; Filing Date Mar. 24, 2015; European Search Report; dated Jul. 14, 2017; 7 pages.
Kuwabara, N., et al., Autoantibodies to lens epithelium-derived growth factor/transcription co-activator P75 (LEDGF/P75) in children with chronic nonspecific complaints and with positive nuclear antiboies, Autoimmunity, Sep. 2009, vol. 12, No. 6, pp. 493-496.
Vandekerckhove, L., et al., Transient and Stable Knockdown of the Integrase Cofactor LEDGF/p75 Reveals Its Role in the Replication Cycle of Human Immunodeficiency Virus, Journal of Virology, Feb. 2006, vol. 80, No. 4, pp. 1886-1896.
Fadel et al., TALEN Knockout of the PSIP1 Gene in Human Cells: Analyses of HIV-1 Replication and Allosteric Integrase Inhibitor Mechanism, J. Virology, Sep. 2014, vol. 88, No. 17, pp. 9704-9717. Sep. 2014.
Mahler et al., The Clinical Significance of the Dense Fine Speckled Immunofluorescence Pattern on HEp-2 Cells for the Diagnosis of Systemic Autoimmune Diseases, Clinical and Developmental Immunology, vol. 2012, Article ID 494356, 6 pages. 2012.
Basu et al.; DFS70/LEDGFp75: An Enigmatic Autoantigen at the Interface Between Autoimmunity, AIDS and Cancer; Frontiers in Immunology; vol. 6; Article 116; Mar. 20, 2015 (5 pages).
EP 15768594.2; Filed Mar. 24, 2015; Office Action dated Jun. 19, 2018 (5 pages).

\* cited by examiner

*Primary Examiner* — Celine X Qian
(74) *Attorney, Agent, or Firm* — Lathrop Gage L.L.P.

(57) ABSTRACT

Provided are compositions that contain mammalian cells for use in detecting antibodies. The mammalian cells are modified such that they do not contain LEDGF protein. The mammalian cells are immobilized on a solid substrate. The compositions can also contain mammalian cells that contain the LEDGF protein. Methods for using the cell compositions in diagnostic approaches are included, as are kits for performing diagnostic tests.

8 Claims, 1 Drawing Sheet
Specification includes a Sequence Listing.

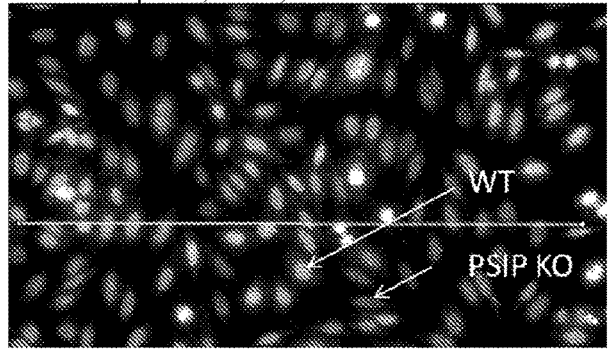
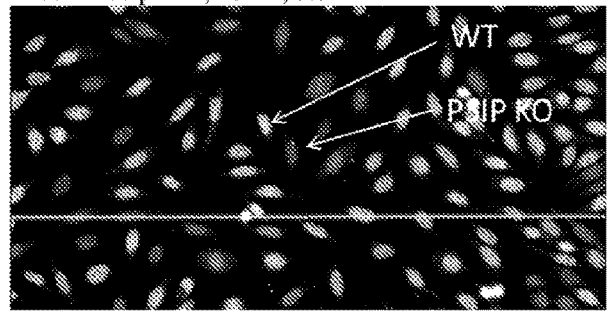
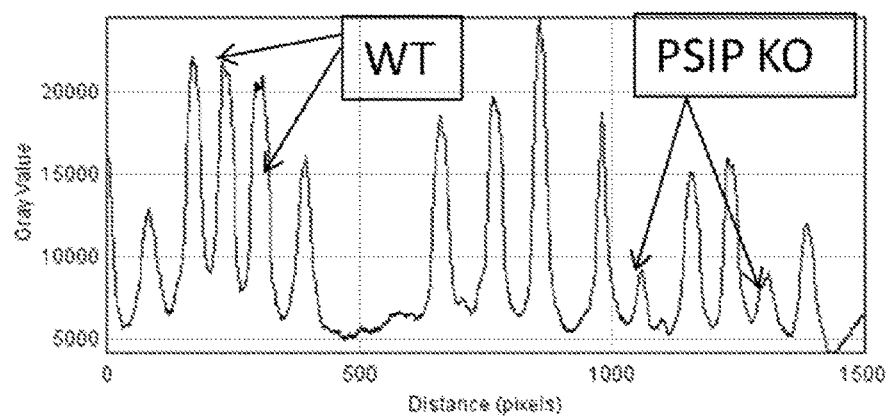
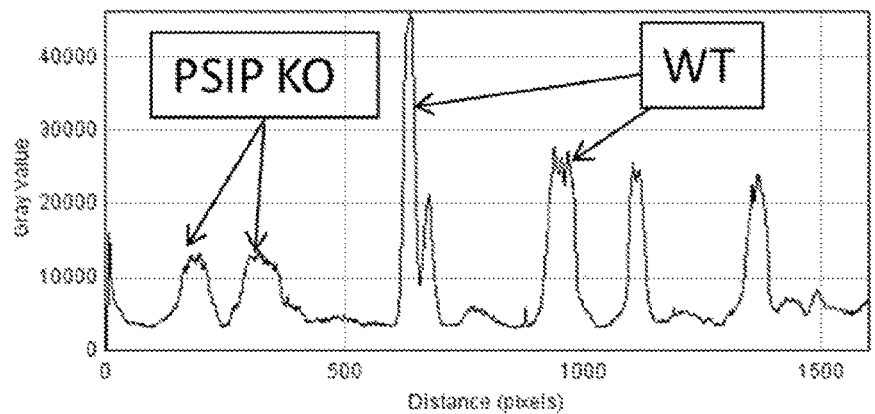

SEQUENCE LISTING

```
<160> NUMBER OF SEQ ID NOS: 16

<210> SEQ ID NO 1
<211> LENGTH: 530
<212> TYPE: PRT
<213> ORGANISM: Homo sapien

<400> SEQUENCE: 1

Met Thr Arg Asp Phe Lys Pro Gly Asp Leu Ile Phe Ala Lys Met Lys
1               5                   10                  15

Gly Tyr Pro His Trp Pro Ala Arg Val Asp Glu Val Pro Asp Gly Ala
                20                  25                  30

Val Lys Pro Pro Thr Asn Lys Leu Pro Ile Phe Phe Phe Gly Thr His
            35                  40                  45

Glu Thr Ala Phe Leu Gly Pro Lys Asp Ile Phe Pro Tyr Ser Glu Asn
        50                  55                  60

Lys Glu Lys Tyr Gly Lys Pro Asn Lys Arg Lys Gly Phe Asn Glu Gly
65                  70                  75                  80

Leu Trp Glu Ile Asp Asn Asn Pro Lys Val Lys Phe Ser Ser Gln Gln
                85                  90                  95

Ala Ala Thr Lys Gln Ser Asn Ala Ser Ser Asp Val Glu Val Glu Glu
            100                 105                 110

Lys Glu Thr Ser Val Ser Lys Glu Asp Thr Asp His Glu Glu Lys Ala
        115                 120                 125

Ser Asn Glu Asp Val Thr Lys Ala Val Asp Ile Thr Thr Pro Lys Ala
130                 135                 140

Ala Arg Arg Gly Arg Lys Arg Lys Ala Glu Lys Gln Val Glu Thr Glu
145                 150                 155                 160

Glu Ala Gly Val Val Thr Thr Ala Thr Ala Ser Val Asn Leu Lys Val
                165                 170                 175

Ser Pro Lys Arg Gly Arg Pro Ala Ala Thr Glu Val Lys Ile Pro Lys
            180                 185                 190

Pro Arg Gly Arg Pro Lys Met Val Lys Gln Pro Cys Pro Ser Glu Ser
        195                 200                 205

Asp Ile Ile Thr Glu Glu Asp Lys Ser Lys Lys Lys Gly Gln Glu Glu
    210                 215                 220

Lys Gln Pro Lys Lys Gln Pro Lys Lys Asp Glu Gly Gln Lys Glu
225                 230                 235                 240

Glu Asp Lys Pro Arg Lys Glu Pro Asp Lys Lys Glu Gly Lys Lys Glu
                245                 250                 255

Val Glu Ser Lys Arg Lys Asn Leu Ala Lys Thr Gly Val Thr Ser Thr
            260                 265                 270

Ser Asp Ser Glu Glu Glu Gly Asp Asp Gln Glu Gly Glu Lys Lys Arg
        275                 280                 285

Lys Gly Gly Arg Asn Phe Gln Thr Ala His Arg Arg Asn Met Leu Lys
    290                 295                 300
```

```
Gly Gln His Glu Lys Glu Ala Ala Asp Arg Lys Arg Lys Gln Glu Glu
305                 310                 315                 320

Gln Met Glu Thr Glu Gln Asn Lys Asp Glu Gly Lys Lys Pro Glu
            325                 330                 335

Val Lys Lys Val Glu Lys Arg Glu Thr Ser Met Asp Ser Arg Leu
        340                 345                 350

Gln Arg Ile His Ala Glu Ile Lys Asn Ser Leu Lys Ile Asp Asn Leu
            355                 360                 365

Asp Val Asn Arg Cys Ile Glu Ala Leu Asp Glu Leu Ala Ser Leu Gln
    370                 375                 380

Val Thr Met Gln Gln Ala Gln Lys His Thr Glu Met Ile Thr Thr Leu
385                 390                 395                 400

Lys Lys Ile Arg Arg Phe Lys Val Ser Gln Val Ile Met Glu Lys Ser
                405                 410                 415

Thr Met Leu Tyr Asn Lys Phe Lys Asn Met Phe Leu Val Gly Glu Gly
            420                 425                 430

Asp Ser Val Ile Thr Gln Val Leu Asn Lys Ser Leu Ala Glu Gln Arg
        435                 440                 445

Gln His Glu Glu Ala Asn Lys Thr Lys Asp Gln Gly Lys Lys Gly Pro
    450                 455                 460

Asn Lys Lys Leu Glu Lys Glu Gln Thr Gly Ser Lys Thr Leu Asn Gly
465                 470                 475                 480

Gly Ser Asp Ala Gln Asp Gly Asn Gln Pro Gln His Asn Gly Glu Ser
            485                 490                 495

Asn Glu Asp Ser Lys Asp Asn His Glu Ala Ser Thr Lys Lys Pro
        500                 505                 510

Ser Ser Glu Glu Arg Glu Thr Glu Ile Ser Leu Lys Asp Ser Thr Leu
    515                 520                 525

Asp Asn
    530

<210> SEQ ID NO 2
<211> LENGTH: 107
<212> TYPE: PRT
<213> ORGANISM: Homo sapien

<400> SEQUENCE: 2

Asp Ser Arg Leu Gln Arg Ile His Ala Glu Ile Lys Asn Ser Leu Lys
1               5                   10                  15

Ile Asp Asn Leu Asp Val Asn Arg Cys Ile Glu Ala Leu Asp Glu Leu
            20                  25                  30

Ala Ser Leu Gln Val Thr Met Gln Gln Ala Gln Lys His Thr Glu Met
        35                  40                  45

Ile Thr Thr Leu Lys Lys Ile Arg Arg Phe Lys Val Ser Gln Val Ile
    50                  55                  60

Met Glu Lys Ser Thr Met Leu Tyr Asn Lys Phe Lys Asn Met Phe Leu
65                  70                  75                  80

Val Gly Glu Gly Asp Ser Val Ile Thr Gln Val Leu Asn Lys Ser Leu
                85                  90                  95

Ala Glu Gln Arg Gln His Glu Glu Ala Asn Lys
            100                 105

<210> SEQ ID NO 3
<211> LENGTH: 1593
<212> TYPE: DNA
```

<213> ORGANISM: Homo sapien

<400> SEQUENCE: 3

| | | | | | |
|---|---|---|---|---|---|
| atgactcgcg | atttcaaacc | tggagacctc | atcttcgcca | agatgaaagg | ttatccccat | 60 |
| tggccagctc | gagtagacga | agttcctgat | ggagctgtaa | agccacccac | aaacaaacta | 120 |
| cccattttct | tttttggaac | tcatgagact | gcttttttag | gaccaaagga | tatatttcct | 180 |
| tactcagaaa | ataaggaaaa | gtatggcaaa | ccaaataaaa | gaaaaggttt | taatgaaggt | 240 |
| ttatgggaga | tagataacaa | tccaaaagtg | aaattttcaa | gtcaacaggc | agcaactaaa | 300 |
| caatcaaatg | catcatctga | tgttgaagtt | gaagaaaagg | aaactagtgt | ttcaaaggaa | 360 |
| gataccgacc | atgaagaaaa | agccagcaat | gaggatgtga | ctaaagcagt | tgacataact | 420 |
| actccaaaag | ctgccagaag | ggggagaaag | agaaaggcag | aaaaacaagt | agaaactgag | 480 |
| gaggcaggag | tagtgacaac | agcaacagca | tctgttaatc | taaaagtgag | tcctaaaaga | 540 |
| ggacgacctg | cagctacaga | agtcaagatt | ccaaaaccaa | gaggcagacc | caaaatggta | 600 |
| aaacagccct | gtccttcaga | gagtgacatc | attactgaag | aggacaaaag | taagaaaaag | 660 |
| gggcaagagg | aaaaacaacc | taaaaagcag | cctaagaagg | atgaagaggg | ccagaaggaa | 720 |
| gaagataagc | caagaaaaga | gccggataaa | aagaggggga | gaaagaagt | tgaatcaaaa | 780 |
| aggaaaaatt | tagctaaaac | aggggttact | tcaacctccg | attctgaaga | agaaggagat | 840 |
| gatcaagaag | tgaaaagaa | gagaaaaggt | gggaggaact | ttcagactgc | tcacagaagg | 900 |
| aatatgctga | aggccaaca | tgagaaagaa | gcagcagatc | gaaaacgcaa | gcaagaggaa | 960 |
| caaatggaaa | ctgagcagca | gaataaagat | gaaggaaaga | agccagaagt | taagaaagtg | 1020 |
| gagaagaagc | gagaaacatc | aatggattct | cgacttcaaa | ggatacatgc | tgagattaaa | 1080 |
| aattcactca | aaattgataa | tcttgatgtg | aacagatgca | ttgaggcctt | ggatgaactt | 1140 |
| gcttcacttc | aggtcacaat | gcaacaagct | cagaaacaca | cagagatgat | tactacactg | 1200 |
| aaaaaaatac | ggcgattcaa | agttagtcag | gtaatcatgg | aaaagtctac | aatgttgtat | 1260 |
| aacaagttta | agaacatgtt | cttggttggt | gaaggagatt | ccgtgatcac | ccaagtgctg | 1320 |
| aataaatctc | ttgctgaaca | aagacagcat | gaggaagcga | ataaaaccaa | agatcaaggg | 1380 |
| aagaaagggc | caaacaaaaa | gctagagaag | gaacaaacag | ggtcaaagac | tctaaatgga | 1440 |
| ggatctgatg | ctcaagatgg | taatcagcca | caacataacg | gggagagcaa | tgaagacagc | 1500 |
| aaagacaacc | atgaagccag | cacgaagaaa | aagccatcca | gtgaagagag | agagactgaa | 1560 |
| atatctctga | aggattctac | actagataac | tag | | | 1593 |

<210> SEQ ID NO 4
<211> LENGTH: 19
<212> TYPE: DNA
<213> ORGANISM: artificial sequence
<220> FEATURE:
<223> OTHER INFORMATION: DNA equivalent of shRNA sequences

<400> SEQUENCE: 4
agacagcatg aggaagcga                                                19

<210> SEQ ID NO 5
<211> LENGTH: 47
<212> TYPE: DNA
<213> ORGANISM: artificial sequence
<220> FEATURE:
<223> OTHER INFORMATION: DNA equivalent of shRNA sequences

<400> SEQUENCE: 5
agacagcatg aggaagcgat tcaagagatc gcttcctcat gctgtct    47

<210> SEQ ID NO 6
<211> LENGTH: 21
<212> TYPE: DNA
<213> ORGANISM: artificial sequence
<220> FEATURE:
<223> OTHER INFORMATION: DNA equivalent of shRNA sequences

<400> SEQUENCE: 6
agttcctgat ggagctgtaa a    21

<210> SEQ ID NO 7
<211> LENGTH: 46
<212> TYPE: DNA
<213> ORGANISM: artificial sequence
<220> FEATURE:
<223> OTHER INFORMATION: DNA equivalent of shRNA sequences

<400> SEQUENCE: 7
agttcctgat ggagctgtaa acgagtttac agctccatca ggaact    46

<210> SEQ ID NO 8
<211> LENGTH: 21
<212> TYPE: DNA
<213> ORGANISM: artificial sequence
<220> FEATURE:
<223> OTHER INFORMATION: DNA equivalent of shRNA sequences

<400> SEQUENCE: 8
gcaatgaaga cagcaaagac a    21

<210> SEQ ID NO 9
<211> LENGTH: 46
<212> TYPE: DNA
<213> ORGANISM: artificial sequence
<220> FEATURE:
<223> OTHER INFORMATION: DNA equivalent of shRNA sequences

<400> SEQUENCE: 9
gcaatgaaga cagcaaagac acgagtgtct ttgctgtctt cattgc    46

<210> SEQ ID NO 10
<211> LENGTH: 21
<212> TYPE: DNA
<213> ORGANISM: artificial sequence
<220> FEATURE:
<223> OTHER INFORMATION: DNA equivalent of shRNA sequences

<400> SEQUENCE: 10
gtctccacgc gcagtacatt t    21

<210> SEQ ID NO 11
<211> LENGTH: 46
<212> TYPE: DNA
<213> ORGANISM: artificial sequence
<220> FEATURE:
<223> OTHER INFORMATION: DNA equivalent of shRNA sequences

<400> SEQUENCE: 11
gtctccacgc gcagtacatt tcgagaaatg tactgcgcgt ggagac    46

<210> SEQ ID NO 12
<211> LENGTH: 454
<212> TYPE: DNA

<213> ORGANISM: Homo sapien

<400> SEQUENCE: 12

| gtacaaaaaa gcaggcttta aaggaaccaa ttcagtcgac tggatccggt accaaggtcg | 60 |
| ggcaggaaga gggcctattt cccatgattc cttcatattt gcatatacga tacaaggctg | 120 |
| ttagagagat aattagaatt aatttgactg taaacacaaa gatattagta caaaatacgt | 180 |
| gacgtagaaa gtaataattt cttgggtagt ttgcagtttt aaaattatgt tttaaaatgg | 240 |
| actatcatat gcttaccgta acttgaaagt atttcgattt cttggcttta tatatcttgt | 300 |
| ggaaaggacg aaacaccgta atcagccaca ataacgtt ttagagctag aaatagcaag | 360 |
| ttaaaataag gctagtccgt tatcaacttg aaaagtggc accgagtcgg tgctttttt | 420 |
| ctagacccag ctttcttgta caagttggc atta | 454 |

<210> SEQ ID NO 13
<211> LENGTH: 455
<212> TYPE: DNA
<213> ORGANISM: Homo sapien

<400> SEQUENCE: 13

| tgtacaaaaa agcaggcttt aaaggaacca attcagtcga ctggatccgg taccaaggtc | 60 |
| gggcaggaag agggcctatt tcccatgatt ccttcatatt tgcatatacg atacaaggct | 120 |
| gttagagaga taattagaat taatttgact gtaaacacaa agatattagt acaaaatacg | 180 |
| tgacgtagaa agtaataatt tcttgggtag tttgcagttt taaaattatg ttttaaaatg | 240 |
| gactatcata tgcttaccgt aacttgaaag tatttcgatt tcttggcttt atatatcttg | 300 |
| tggaaaggac gaaacaccga cgcctctgcg gcagctgggt tttagagcta gaaatagcaa | 360 |
| gttaaaataa ggctagtccg ttatcaactt gaaaagtgg caccgagtcg gtgcttttt | 420 |
| tctagaccca gctttcttgt acaaagttgg catta | 455 |

<210> SEQ ID NO 14
<211> LENGTH: 455
<212> TYPE: DNA
<213> ORGANISM: Homo sapien

<400> SEQUENCE: 14

| tgtacaaaaa agcaggcttt aaaggaacca attcagtcga ctggatccgg taccaaggtc | 60 |
| gggcaggaag agggcctatt tcccatgatt ccttcatatt tgcatatacg atacaaggct | 120 |
| gttagagaga taattagaat taatttgact gtaaacacaa agatattagt acaaaatacg | 180 |
| tgacgtagaa agtaataatt tcttgggtag tttgcagttt taaaattatg ttttaaaatg | 240 |
| gactatcata tgcttaccgt aacttgaaag tatttcgatt tcttggcttt atatatcttg | 300 |
| tggaaaggac gaaacaccga ggtagacgaa gttcctgagt tttagagcta gaaatagcaa | 360 |
| gttaaaataa ggctagtccg ttatcaactt gaaaagtgg caccgagtcg gtgcttttt | 420 |
| tctagaccca gctttcttgt acaaagttgg catta | 455 |

<210> SEQ ID NO 15
<211> LENGTH: 455
<212> TYPE: DNA
<213> ORGANISM: Homo sapien

<400> SEQUENCE: 15

| tgtacaaaaa agcaggcttt aaaggaacca attcagtcga ctggatccgg taccaaggtc | 60 |
| gggcaggaag agggcctatt tcccatgatt ccttcatatt tgcatatacg atacaaggct | 120 |

```
gttagagaga taattagaat taatttgact gtaaacacaa agatattagt acaaaatacg    180
tgacgtagaa agtaataatt tcttgggtag tttgcagttt taaaattatg tttttaaaatg   240 gactatcata tgcttaccgt aacttgaaag tatttcgatt tcttggcttt atatatcttg   300
tggaaaggac gaaacaccga actacccatt ttcttttttgt tttagagcta gaaatagcaa   360
gttaaaataa ggctagtccg ttatcaactt gaaaaagtgg caccgagtcg gtgctttttt   420
tctagaccca gctttcttgt acaaagttgg catta                              455

<210> SEQ ID NO 16
<211> LENGTH: 455
<212> TYPE: DNA
<213> ORGANISM: Homo sapien

<400> SEQUENCE: 16
tgtacaaaaa agcaggcttt aaaggaacca attcagtcga ctggatccgg taccaaggtc     60
gggcaggaag agggcctatt tcccatgatt ccttcatatt tgcatatacg atacaaggct   120
gttagagaga taattagaat taatttgact gtaaacacaa agatattagt acaaaatacg   180
tgacgtagaa agtaataatt tcttgggtag tttgcagttt taaaattatg tttttaaaatg   240 gactatcata tgcttaccgt aacttgaaag tatttcgatt tcttggcttt atatatcttg   300
tggaaaggac gaaacaccga gtgctttttt aggaccaagt tttagagcta gaaatagcaa   360
gttaaaataa ggctagtccg ttatcaactt gaaaaagtgg caccgagtcg gtgctttttt   420
tctagaccca gctttcttgt acaaagttgg catta                              455
```

ANTI-NUCLEAR ANTIBODY DETECTION AND DIAGNOSTICS FOR SYSTEMIC AND NON-SYSTEMIC AUTOIMMUNE DISORDERS

CROSS REFERENCE TO RELATED APPLICATIONS

This application claims priority to U.S. provisional application No. 61/969,771, filed on Mar. 24, 2014, the disclosure of which is incorporated herein by reference.

FIELD

The present invention relates generally to autoimmune disease and more particularly to compositions and methods for use in detecting anti-nuclear antibodies

BACKGROUND

Autoimmune diseases are typically challenging to diagnose, and in general individuals with one autoimmune disease are at higher risk for developing others, such as systemic autoimmune rheumatic diseases (SARDs). The presence of anti-nuclear autoantibodies (ANAs) is considered to be a hallmark of SARDS, and this association has been known for some time. The American College of Rheumatology (ACR) recommends testing for ANAs by indirect immunofluorescence (IIF) assay using HEp-2 cells, as described in their position statement in 2009. This statement explained that HEp-2 cells are able to express 100-150 relevant auto-antigens for use in ANA antibody detection. Thus, immobilized and preserved monolayers of HEp2 cells are the most commonly used substrates in IIF detection of ANAs.

ANA detection using IIF assay can reveal a multitude of patterns such as homogeneous, fine granular, coarse granular, nucleolar, centromere, nuclear dots, pleomorphic, mitochondrial and a variety of cytoskeletal patterns. Patients can have one or more patterns in combination with varying intensity of reactivity for each pattern. These patterns are a result of specific autoantibody binding to nuclear and cytoplasmic antigens which include but are not necessarily limited to dsDNA, nucleosomes, histones, SS-A Ro52/Ro60, SS-B/La, Ku, Mi-2, RNPs (Ribonucleoproteins: U1SnRNP 68, U1SnRNP A, U1SnRNP C, U2SnRNPs etc,), Sc1-70, PM-Scl, Fibrillarin, Th/To, CENP-B, CENP-A, Sp100, PCNA, Ribo-P, Jo1, AMA-M2, Actin, Vimentin, and others.

Other methodologies have been utilized for screening and confirmation of ANAs. However, due to a variety of reasons, which include but are not limited to prevalence of false negative and false positive results, lack of standardization of test algorithms (i.e., reflex testing), and an inability to detect the diverse arrays of ANAs prevalent in individuals with SARDS, use of HEp-2 cells as the substrate for ANA testing remains the gold standard. Unfortunately, use of HEp-2 cells also involves complex test interpretation, false results and specialized skills, in part because it has been reported that up to 20% of apparently healthy subjects give a positive ANA IIF test result due to the presence of autoantibodies that recognize the so-called "dense fine speckles 70" (DFS70) antigen, which is also referred to herein and in the art as lens epithelium-derived growth factor (LEDGF). PSIP1/LEDGF is also known as AA408851, AU015605, Dfs70, Ledgf, Ledgfa, Ledgfb, mLEDGF, PC4 and SFRS1-interacting protein (PSIP1), Psip2 (isoform), p52, p75, PAIP encoded by the PSIP1 gene. Moreover, the DFS IIF pattern has been reported in up to 20% of ANA positive healthy subjects, but often not in ANA positive sera obtain from SARD patients (Mahler and Fritzler 2012). Since the main objective of the ANA HEp-2 test is to function as a tool for diagnosing and classifying SARD, as well as potentially other autoimmune diseases, the anti-DFS70 antibodies and the DFS pattern they produce reduce the usefulness of the ANA test, such as by increasing false results and otherwise complicating test interpretation. This has important ramifications for a variety of approaches that rely on accurate detection of ANA and treatment decisions for patients who are tested for ANA antibodies. Thus, there is an ongoing and unmet need for improved compositions and methods for detecting ANA. The present disclosure meets these and other needs.

SUMMARY

The present disclosure comprises in various embodiments compositions and methods for use in detecting ANA autoantibodies, and/or for determining whether a biological sample obtained or derived from an individual comprises antibodies that recognize the LEDGF protein. The disclosure includes compositions and methods that can be used for diagnosing and/or aiding in the diagnosis of autoimmune disorders that are positively correlated with the presence of ANA autoantibodies. Kits/products comprising reagents for use in detection of ANA autoantibodies, such as antibodies to LEDGF protein, are also provided In one aspect the present disclosure comprises modified mammalian cells for use in detecting antibodies. The mammalian cells are modified such that they do not express or comprise LEDGF protein (LEDGF− cells). In embodiments, the disclosure includes mixtures of the mammalian LEDGF− cells, and mammalian cells that do express and comprise LEDGF protein (LEDGF+ cells). In embodiments, the mammalian cells are immobilized on a solid substrate, such as a glass, plastic, or other polymer-based substrate. In embodiments, the solid substrate comprises a microscope slide, a diagnostic slide, a microtitre plate, or beads formed of glass or a polymer.

In embodiments, the cells are killed and permeabilized. Those skilled in the art will recognize that permeabilized cells are those cells which have been exposed to organic reagents (commonly referred to in the art as 'fixatives') which can include but are not limited to organic solvents, such as acetone, alcohol, and aldehyde containing solutions, such as formaldehyde, paraformaldehyde, and the like. Cells exposed to such reagents are commonly referred to as "fixed" and the process of treating them with such reagents is referred to as "fixing" the cells. Fixing the mammalian cells such that they are permeabilized is lethal, and thus the fixed/permeabilized cells are also considered to be killed cells.

The LEDGF− cells are modified using any suitable techniques, reagents and the like such that LEDGF protein is not expressed, or its expression is reduced. In embodiments, mRNA encoding the LEDGF protein is degraded using any of a variety of RNAi-mediated approaches. In another embodiment, the gene encoding the LEDGF protein, which is described more fully below, is disrupted by any suitable technique including but not limited to the use of a clustered regularly interspaced short palindromic repeats (CRISPR) system comprising a CRISPR-associated (Cas) nuclease and a CRISPR guide RNA (gRNA). In embodiments, the modification to the cells comprises integration of a polynucleotide sequence encoding the Cas enzyme and/or the gRNA into at least one chromosome of the cells, such as the LEDGF− cells.

In embodiments, the compositions and methods use modified LEDGF+ and LEDGF− cells of the same type, i.e., they are both the same type of cancer cell, or they are both of the same cell line, or derived from the same cell line.

In embodiments the disclosure includes mixtures of LEDGF+ mammalian cells and modified LEDGF− mammalian cells that are useful in diagnostic assays. The mixtures can be such that antibodies that bind to antigens in the modified cells can be used to, for example, establish a background amount of antibody binding that can be compared to antibody binding using the LEDGF+ cells as a comparison substrate. Thus, in certain aspects, a ratio of LEDGF− and LEDGF+ cells are provided. In embodiments, the ratio comprises a LEDGF− cell amount to a LEDGF+ cell amount of 1:1, 1:2, 1:3, 1:4, 1:3, 1:6, 1:7, 1:8, 1:9, 1:10, as well as the reverse ratios.

In embodiments the disclosure includes modified cells, wherein the modification is such that the cells do not express LEDGF, cell cultures/cell lines derived from such cells, and their progeny.

In embodiments the disclosure includes LEDF+ cells, wherein the LEDGF protein in the LEGDF+ cells is present in a complex with an antibody, and thus is suitable for use in a variety of immuno-diagnostic tests. In an embodiment, the antibody is a first antibody, such as a primary antibody. In embodiments, the primary antibody that is bound the LEDGF protein the LEDGF+ cells is itself present in a complex with a detectably labeled secondary antibody.

In embodiments, the LEDGF+ and/or LEDGF− cells comprise one or more nuclear antigens in present in a complex with an antibody.

In another aspect the disclosure provides a method for determining whether a biological sample comprises antibodies that bind to LEDGF protein (anti-LEDGF Abs). The method generally comprises the steps of:
  i) exposing the biological sample to mammalian cells that are modified such that they do not comprise LEDGF protein (LEDGF− cells),
  ii) exposing the biological sample to mammalian cells that comprise the LEDGF protein (LEDGF+ cells), and
  iii) comparing the amount of anti-LEDGF Abs bound to the LEDGF− cells to the amount of anti-LEDGF Abs bound to the LEDGF+ cells,
  wherein determining a greater amount of anti-LEDGF Abs bound to the LEDGF+ cells relative to the amount of anti-LEDGF Abs bound to the LEDGF −cells is indicative that the biological sample comprised the anti-LEDGF Abs, and
  wherein the same or less anti-LEDGF Abs bound to the LEDGF+ cells relative to the amount of anti-LEDGF Abs bound to the LEDGF− cells is indicative that the biological sample did not comprise the anti-LEDGF Abs.

In embodiments, the cells used in the method are killed and permeabilized and are immobilized on a solid substrate. In embodiments, the LEDGF− cells and the LEDGF+ cells are immobilized on the same solid substrate; in embodiments they are immobilized on distinct solid substrates. In embodiments, determining the amount of anti-LEDGF Abs is performed using an indirect immunofluorescence (IIF) assay.

In another aspect the disclosure comprises a kit comprising modified LEDGF− cells and LEDGF+ cells, wherein the LEDGF− cells and the LEDGF+ cells are immobilized on one or more solid substrates, and wherein the LEDGF− cells and the LEDGF+ cells are killed and permeabilized. In embodiments, the solid substrate(s) and the cells are dried, and are provided in one or more suitable containers.

In embodiments, the kit further comprises a composition comprising primary antibodies that are capable of binding to anti-nuclear autoantibodies (ANAs). The kit may further comprise detectably labeled secondary antibodies that are capable of binding to the primary antibodies. Any suitable detectable label can be used and many are well known in the art. In embodiments, the detectable label is a florescent label and is thus suitable for use in, for example, an IIF assay.

BRIEF DESCRIPTION OF THE FIGURE

FIG. 1: Wild Type Hep2 expressing LEDGF and PISP1 disrupted cell line using per Example Sequence 3 and not expressing LEDGF were tested by IIF using confirmed human DFS70 positive anti-sera. Top panel: two examples (A1 and B1) show brightly labeled cells (WT) and cells with background fluorescence signal (PSIP KO). Bottom panel: profile analysis (ImageJ version 1.421, National Institute of Health, USA) plots the intensity of labeled nuclei along the line (A2 is intensity plot for A1; B2 is intensity plot for B1). High peaks correspond to WT cells and low peaks correspond to PSIP-KO cells which do not express any detectable LEDGF protein.

DETAILED DESCRIPTION

The present disclosure provides compositions and methods for using the compositions in detecting ANA autoantibodies, and/or for determining whether a biological sample obtained or derived from an individual comprises antibodies that recognize the LEDGF protein, and for diagnosing and/or aiding in the diagnosis of autoimmune disorders that are positively correlated with the presence of ANA autoantibodies. Such disorders include but not necessarily limited to systemic autoimmune rheumatic diseases (SARDs). Kits/products comprising reagents for use in detection of ANA autoantibodies are also provided.

In general, the disclosure provides approaches to reducing and/or eliminating the DFS pattern that is frequently characteristic of IIF analysis of ANAs that in current testing typically rely on HEp-2 cells as a substrate, and encompasses in vitro compositions comprising modified mammalian cells that have less LEDGF expression relative to unmodified HEp-2 cells, and methods of using such modified cells to detect ANA autoantibodies. However, rather than being limited to modified HEp-2 cells, the present disclosure provides compositions comprising mammalian cells of any origin, wherein the cells have been modified to be improved substrates for ANA and/or LEDGF testing. Thus, in various embodiments, the present disclosure involves mammalian cells that comprise the PSIP1 gene, and to at least some degree express the LEDGF protein encoded by the PSIP1 gene, but subsequent to being modified as more fully described below, express less LEDGF protein relative to unmodified cells of the same type, or do not express any detectable LEDGF protein. It will be recognized by those skilled in the art that most mammalian cells express LEDGF, and thus it is expected that cells used in compositions and methods of this disclosure can include cells of any mammalian cell line, or cells derived from any mammalian cell line, or any other suitable source. In embodiments, the cells are immortalized. In embodiments, the cells are progeny of a cell line derived from cancer, such as a tumor. In embodiments, the cells are multiploid and as such have more than two copies of at least one chromosome. In embodiments, the cells comprise more than two copies of a chromosome that comprises the PSIP1 gene, which as described further below encodes the LEDGF protein. In embodiments, the cells are aneuploid, and may be pseudo hypotripoloid. In embodiments, the cells are derived from human cells and comprise more than 23 distinct chromosomes. In embodiments, the disclosure provides modified cell lines that are altered such that expression of the LEDGF protein is reduced or eliminated. In embodiments, the disclosure provides modifications of known cell lines, such as cell lines that can be grown in monolayers and fixed, including but not necessarily limited to HEp-2 and HeLa cells. In embodiments, cell types that can be modified for use with the present disclosure are commercially available from sources, such as the American Type Culture Collection (ATCC). In non-limiting embodiments the cells are HEp2 or HeLa cells. These cells are available from ATCC as catalog # CCL-23 for HEp2, and CCL-2 or CCL-2.2 for HeLa adherent and suspension cultures respectively. As described above, in embodiments, the disclosure includes cells that are modified such that they express no detectable LEDGF protein, or express less LEDGF protein than cells of the same type. Thus, it will be recognized that cells of the same type can comprise, as one non-limiting example, HEp2 cells, wherein the modified HEp2 cells express less LEDGF protein than unmodified HEp2 cells, wherein the HEp2 cells are the "type" of cells that are described. The same applies to any other mammalian cells, wherein the unmodified cells express detectable LEDGF, including but not limited to HeLa cells, and other cell lines derived from, for example, blood plasma cells, monocytes, neutrophils, T-lymphocytes, platelets, T-cell leukemia cells, myeloid leukemia cells, lymphoblastic leukemia cells, kidney cells, kidney cancer cells, liver cells, liver cancer cells, lung cells, lung cancer cells, colon cells, colon cancer cells, heart cells, bone cells, bone cancer cells, brain cells, brain cancer cells, ovary cells, ovarian cancer cells, prostate cells, prostate cancer cells, cervical cells, cervical cancer cells, melanoma, breast tissue cells, breast cancer cells, skin cells, melanoma cells, pancreatic cells and pancreatic cancer cells, and others.

Approaches to immunodiagnostic assays provided in this disclosure involve modifying mammalian cells to cause down-regulation or elimination of the PSIP1/LEDGF gene product, and methods of using the modified cells in autoimmune assays. The disclosure also includes the modified cells, and compositions comprising the modified, such as cell cultures. Kits for use in the assays are also provided.

As described above, the DFS pattern is well known in the art and comprises a dense fine speckled pattern resulting from autoantibodies that specifically bind to LEDGF protein (Ayaki, Sueno et al. 1999). Autoantibodies to LEDGF protein were first reported in association with atopic dermatitis and other conditions such as Asthma, interstitial cystitis (Ochs, Muro et al. 2000), alopecia areata (Okamoto, Ogawa et al. 2004) and in 0-20% of healthy individuals (Watanabe, Kodera et al. 2004, Mahler, Parker et al. 2012). LEDGF belongs to a selected group of autoantigens that are targeted for cleavage during cell death, and it has been proposed that the caspase-induced LEDGF cleavage and the generation of autoantibodies to the protein might contribute to the pathogenesis of various human atopic and inflammatory disorders associated with deregulated apoptosis (Ganapathy, Daniels et al. 2003, Ganapathy and Casiano 2004). LEDGF protein has also been implicated in HIV integration, and LEDGF has been knocked down both transiently (using siRNA) and stably (using shRNA followed by selection) resulting in a 3-5 fold reduction in HIV-1 replication in HeLaP4 cells (Vandekerckhove, Christ et al. 2006).

The amino acid sequence of the LEDGF protein is known in the art and the canonical sequence is provided here as SEQ ID NO:1:

```
                                              (SEQ ID NO: 1)
MTRDFKPGDLIFAKMKGYPHWPARVDEVPDGAVKPPTNKLPIFFFGTHET

AFLGPKDIFPYSENKEKYGKPNKRKGFNEGLWEIDNNPKVKFSSQQAATK

QSNASSDVEVEEKETSVSKEDTDHEEKASNEDVTKAVDITTPKAARRGRK

RKAEKQVETEEAGVVTTATASVNLKVSPKRGRPAATEVKIPKPRGRPKMV

KQPCPSESDIITEEDKSKKKGQEEKQPKKQPKKDEEGQKEEDKPRKEPDK

KEGKKEVESKRKNLAKTGVTSTSDSEEEGDDQEGEKKRKGGRNFQTAHRR

NMLKGQHEKEAADRKRKQEEQMETEQQNKDEGKKPEVKKVEKKRETSMDS

RLQRIHAEIKNSLKIDNLDVNRCIEALDELASLQVTMQQAQKHTEMITTL

KKIRRFKVSQVIMEKSTMLYNKFKNMFLVGEGDSVITQVLNKSLAEQRQH

EEANKTKDQGKKGPNKKLEKEQTGSKTLNGGSDAQDGNQPQHNGESNEDS

KDNHEASTKKKPSSEERETEISLKDSTLDN.
```

Other isoforms and truncated versions which comprise mutations that differ from the canonical sequence are known in the art. In particular, GenBank (NCBI) entries NP_001121689.1, NM_001128217.1, [O75475-1], NP_066967.3, NM_021144.3, [O75475-2], NP_150091.2, NM_033222.3, [O75475-1], XP_005251413.1 provide LEDGF, and the polynucleotide and amino acid sequences described in these database entries are incorporated herein by reference as they exist as of the filing of this application or patent XM_005251356.1, [O75475-2], XP_005251415.1, XM_005251358.1 and [O75475-3].

The immunoreactive sequence of the SEQ ID NO:1 has been reported (Ogawa, Sugiura et al. 2004) to be a polypeptide from amino acid number 349-455 described in SEQ ID NO:2.

```
                                              (SEQ ID NO: 2)
DSRLQRIHAEIKNSLKIDNLDVNRCIEALDELASLQVTMQQAQKHTEMIT
TLKKIRRFKVSQVIMEKSTMLYNKFKNMFLVGEGDSVITQVLNKSLAEQR
QHEEANK.
```

The cDNA sequence encoding LEDGF is also known in the art and is provided here as SEQ ID NO:3.

```
                                              (SEQ ID NO: 3)
ATGACTCGCGATTTCAAACCTGGAGACCTCATCTTCGCCAAGATGAAAGG

TTATCCCCATTGGCCAGCTCGAGTAGACGAAGTTCCTGATGGAGCTGTAA

AGCCACCCACAAACAAACTACCCATTTTCTTTTTTGGAACTCATGAGACT

GCTTTTTTAGGACCAAAGGATATATTTCCTTACTCAGAAAATAAGGAAAA

GTATGGCAAACCAAATAAAAGAAAAGGTTTTAATGAAGGTTTATGGGAGA

TAGATAACAATCCAAAAGTGAAATTTTCAAGTCAACAGGCAGCAACTAAA

CAATCAAATGCATCATCTGATGTTGAAGTTGAAGAAAAGGAAACTAGTGT

TTCAAAGGAAGATACCGACCATGAAGAAAAAGCCAGCAATGAGGATGTGA

CTAAAGCAGTTGACATAACTACTCCAAAAGCTGCCAGAAGGGGGAGAAAG
```

-continued

```
AGAAAGGCAGAAAAACAAGTAGAAACTGAGGAGGCAGGAGTAGTGACAAC

AGCAACAGCATCTGTTAATCTAAAAGTGAGTCCTAAAAGAGGACGACCTG

CAGCTACAGAAGTCAAGATTCCAAAACCAAGAGGCAGACCCAAAATGGTA

AAACAGCCCTGTCCTTCAGAGAGTGACATCATTACTGAAGAGGACAAAAG

TAAGAAAAAGGGGCAAGAGGAAAAACAACCTAAAAAGCAGCCTAAGAAGG

ATGAAGAGGGCCAGAAGGAAGAAGATAAGCCAAGAAAAGAGCCGGATAAA

AAAGAGGGGAAGAAAGAAGTTGAATCAAAAAGGAAAAATTTAGCTAAAAC

AGGGGTTACTTCAACCTCCGATTCTGAAGAAGAAGGAGATGATCAAGAAG

GTGAAAAGAAGAGAAAAGGTGGGAGGAACTTTCAGACTGCTCACAGAAGG

AATATGCTGAAAGGCCAACATGAGAAAGAAGCAGCAGATCGAAAACGCAA

GCAAGAGGAACAAATGGAAACTGAGCAGCAGAATAAAGATGAAGGAAAGA

AGCCAGAAGTTAAGAAAGTGGAGAAGAAGCGAGAAACATCAATGGATTCT

CGACTTCAAAGGATACATGCTGAGATTAAAAATTCACTCAAAATTGATAA

TCTTGATGTGAACAGATGCATTGAGGCCTTGGATGAACTTGCTTCACTTC

AGGTCACAATGCAACAAGCTCAGAAACACACAGAGATGATTACTACACTG

AAAAAAATACGGCGATTCAAAGTTAGTCAGGTAATCATGGAAAAGTCTAC

AATGTTGTATAACAAGTTTAAGAACATGTTCTTGGTTGGTGAAGGAGATT

CCGTGATCACCCAAGTGCTGAATAAATCTCTTGCTGAACAAAGACAGCAT

GAGGAAGCGAATAAAACCAAAGATCAAGGGAAGAAAGGGCCAAACAAAAA

GCTAGAGAAGGAACAAACAGGGTCAAAGACTCTAAATGGAGGATCTGATG

CTCAAGATGGTAATCAGCCACAACATAACGGGGAGAGCAATGAAGACAGC

AAAGACAACCATGAAGCCAGCACGAAGAAAAAGCCATCCAGTGAAGAGAG

AGAGACTGAAATATCTCTGAAGGATTCTACACTAGATAACTAG
```

To provide compositions and methods for improved ANA and/or LEDGF antibody detection for systemic and non-systemic autoimmune diseases (organ specific autoimmune diseases, atopic dermatitis, alopecia etc.,) and differentiation from disease free human population, any suitable mammalian cells, including but not limited to HEp-2 HeLa, HEK293, or a cell line suitable for culturing as adherent (monolayer) or suspension format can be modified in a variety of ways, given the benefit of the present disclosure. In various embodiments LEDGF protein is reduced in the modified cells by reducing mRNA encoding it. In another approach the disclosure includes disrupting the PSIP1 gene from making a protein by via knock-out or targeted mutation. The disclosure also includes making and using modified cells characterized by reduced or eliminated LEDGF protein. In embodiments, the modified cells are also engineered to express a detectable marker, such as a fluorescent protein or an immunoreactive protein that can further be detected using a specific secondary antibody (including but not necessarily limited to a Poly histidine tag, c-Myc tag, FLAG tag etc., which are well characterized in the art).

In one aspect, the disclosure includes reducing LEDGF mRNA, and as a result reducing the LEDGF protein, in modified mammalian cells. In one approach this aspect comprises introducing into the suitable mammalian cells a polynucleotide that can inhibit translation of LEDGF mRNA, and/or can participate in and/or facilitate RNAi-mediated reduction of LEDGF mRNA. In one embodiment, an antisense polynucleotide is used to inhibit translation of LEDGF mRNA. Antisense nucleic acids can be DNA or RNA molecules that are complementary to at least a portion of the LEDGF mRNA. In embodiments, oligomers of about fifteen nucleotides, and/or those that hybridize to the AUG initiation codon will be particularly efficient. The polynucleotides described herein for use in targeting LEDGF mRNA can in certain embodiments be modified, such as to be resistant to nucleases.

In embodiments, the present disclosure provides for replacement of the PSIP1 gene with a sequence encoding a detectable marker, such as a fluorescent protein, or integrating such a sequence into the PSIP1 gene, thereby disrupting it, or integrating such a sequence elsewhere in the genome of the cells. By replacing PSIP1 or integrating a sequence encoding a detectable protein into it the disclosure provides for marking modified mammalian cells which do not express LEDGF. This is valuable in that those cells which express the detectable protein can be selected for use in the immunoassays of the invention, and for including in products that are intended to be used in such immunoassay. In embodiments, disrupting the PSIP1 gene with a sequence encoding a fluorescent protein will allow for enriching a cell population with cells that contain the LEDGF disruption, such as by using FACS to separate cells that contain the disruption from those that do not, thereby providing an isolated and/or purified population of modified cells that do not express LEDGF. The detectable marker can be any protein that can be detected, and is preferably a fluorescent protein. Any fluorescent protein can be used. In embodiment, the fluorescent protein is selected from GFP, eGFP, Red Fluorescent protein or variants thereof such as tRFP, dsRED, mCherry, tdTomato etc.,) or any fluorescent protein that does not interfere with the conjugates used in, for example, an IIF method to detect autoantibodies. Thus, in embodiments, the present disclosure includes cells characterized by having the PSIP1 gene disrupted or knocked out. In embodiments, the knock out comprises a disruption of the gene by introducing (a knock in) of a detectable protein.

In embodiments, the disclosure includes introducing an expression vector which can inhibit LEDGF protein, and which may also express a detectable marker. For example, an expression vector with two distinct promoters or a bidirectional promoter can be used to express shRNA targeted to PSIP1 and express the detectable marker. In alternative embodiments, two distinct expression vectors can be used for this purpose. In embodiments, the vectors are stably or transiently present in the cells. In embodiments, one or both vectors, or the single vector encoding the shRNA and the detectable marker, is integrated into at least one position in a chromosome in a mammalian cell.

In another aspect the disclosure includes RNAi-mediated reduction in LEDGF mRNA. RNAi-based inhibition can be achieved using any suitable RNA polynucleotide that is targeted to LEDGF mRNA. In embodiments, a single stranded or double stranded RNA, wherein at least one strand is complementary to the LEDGF mRNA, can be introduced into the cell to promote RNAi-based degradation of LEDGF mRNA. In another embodiment, microRNA (miRNA) targeted to the LEDGF mRNA can be used. In another embodiment, a ribozyme that can specifically cleave LEDGF mRNA can be used. In yet another embodiment, small interfering RNA (siRNA) can be used. siRNA (or ribozymes) can be introduced directly, for example, as a double stranded siRNA complex, or by using a modified expression vector, such as a lentiviral vector, to produce an shRNA. As is known in the art, shRNAs adopt a typical hairpin secondary structure that contains a paired sense and antisense portion, and a short loop sequence between the paired sense and antisense portions. shRNA is delivered to the cytoplasm where it is processed by DICER into siRNAs. siRNA is recognized by RNA-induced silencing complex (RISC), and once incorporated into RISC, siRNAs facilitate cleavage and degradation of targeted mRNA. In embodiments, an shRNA polynucleotide used to suppress LEDGF expression can comprise or consist of between 45-100 nucleotides, inclusive, and including all integers between 45 and 100. The portion of the shRNA that is complementary to the LEDGF mRNA mRNA can be from 21-29 nucleotides, inclusive, and including all integers between 21 and 29.

For delivering siRNA via shRNA, modified lentiviral vectors can be made and used according to standard techniques, given the benefit of the present disclosure. Further, lentiviral vectors expressing shRNAs targeted to many human mRNAs are commercially available. Additionally, custom siRNAs or shRNA can be obtained from, for example Thermo-Dharmacon for transient transfection resulting in temporary reduction in LEDGF levels. Alternatively, lentiviral constructs expressing human PSIP11 targeted shRNA can be obtained from Thermo Dharmacon. These lentiviruses are capable of stably and permanently infecting target cells, such as by integrating into a chromosome in the cells. However, as will be apparent from the following description, RNAi-mediated approaches for disrupting expression of the LEDGF protein may not be optimal. For example, we introduced DNA sequences encoding shRNAs designed against the PSIP1 gene and cloned them into lenti-viral vectors downstream of a U6 promoter. Lentivirus with the DNA insert capable of producing either target shRNA or negative control were used to infect HEp2 cells. Viral infectivity and titer was measured by an integrated RFP (Red fluorescent protein) marker that is expressed in all the infected cells. The RFP marker was also fused to puromycin (antibiotic) resistance factor which is used for selection of cells that stably incorporated the construct into the genome of HEp2 cells. Examples of tested sequences are below, where the DNA equivalent of the shRNA sequence is provided: shRNA(h PSIP1) example #1 sequence: AGACAGCATGAGGAAGCGA (SEQ ID NO:4).

Cloned shRNA hairpin sequence:

(SEQ ID NO: 5)
AGACAGCATGAGGAAGCGAttcaagagaTCGCTTCCTCATGCTGTCT shRNA(h PSIP1) example #2 sequence:
(SEQ ID NO: 6)
AGTTCCTGATGGAGCTGTAAA Cloned shRNA hairpin sequence:

(SEQ ID NO: 7)
AGTTCCTGATGGAGCTGTAAAcgagTTTACAGCTCCATCAGGAACT hPSIP 1) example #3 sequence:
(SEQ ID NO: 8)
GCAATGAAGACAGCAAAGACA Cloned shRNA hairpin sequence:

(SEQ ID NO: 9)
GCAATGAAGACAGCAAAGACAcgagTGTCTTTGCTGTCTTCATTGC shRNA-Neg-Control:

(SEQ ID NO: 10)
GTCTCCACGCGCAGTACATTT

Cloned shRNA-Neg hairpin sequence:

(SEQ ID NO: 11)
GTCTCCACGCGCAGTACATTTcgagAAATGTACTGCGCGTGGAGAC

IIF analysis using the above sequences (lentiviral transduction procedure followed by selection for resistant colonies) using DFS70 specific antisera indicated a low level decrease in PSIP1/LEDGF levels. Negative controls did not show any reduction in the PSIP1/LEDGF levels using the same procedure. Further, while siRNA can produce an intense reduction in mRNA levels, the effects are usually transient. Thus, even though shRNA technology is compatible with selection processes and allows the isolation of colonies stably expressing the short hairpin RNA, which further aids in the degradation of specific complementary mRNA in subsequent generation of cells, as observed in the aforementioned approaches, the reduction of PSIP1 levels at the mRNA level were not adequate to provide an improved substrate for IIF analysis for use in detecting autoantibodies directed to ANA. Thus, the disclosure includes alternative approaches for disrupting LEDGF protein production. In this regard, the disclosure also includes disrupting the PSIP1 gene with a mutation such that LEDGF mRNA and protein are not expressed. In one embodiment, the PSIP1 gene can be disrupted by targeted mutagenesis. In embodiments, targeted mutagenesis can be achieved by, for example, targeting a CRISPR (clustered regularly interspaced short palindromic repeats) site in the PSIP1 gene. So-called CRISPR systems designed for targeting specific genomic sequences are known in the art and can be adapted to disrupt the PSIP1 gene for making modified cells encompassed by this disclosure. In general, the CRISPR system includes one or more expression vectors encoding at least a targeting RNA and a polynucleotide sequence encoding a CRISPR-associated nuclease, such as Cas9, but other Cas nucleases can be used. CRISPR systems for targeted disruption of mammalian chromosomal sequences are commercially available and can be adapted to disrupt the PSIP1 gene in HEp-2 cells given the benefit of this disclosure.

In embodiments, a targeting RNA encoded by the CRISPR system can be a CRISPR RNA (crRNA) or a guide RNA, such as sgRNA. The sequence of the targeting RNA has a segment that is the same as or complementarity to any CRISPR site in the PSIP1 gene. In this regard, the target sequence comprises a specific sequence on its 3' end referred to as a protospacer adjacent motif or "PAM". In an embodiment a CRISPR Type II system is used, and the target sequences therefore conform to the well-known N12-20NGG motif, wherein the NGG is the PAM sequence. Thus, in embodiments, a target RNA will comprise or consist of a segment that is from 12-20 nucleotides in length which is the same as or complementary to a. DNA target sequence (a spacer) in the PSIP1 gene. The 12-20 nucleotides directed to the spacer sequence will be present in the targeting RNA, regardless of whether the targeting RNA is a crRNA or a guide RNA. In embodiments, a separate trans-activating crRNA (tracrRNA) can be used to assist in maturation of a crRNA targeted to the PSIP1 gene. introduction a CRISPR system into HEp-2 cells will result in binding of a targeting RNA/Cas9 complex to the PSIP1 target sequence so that the Cas9 can cut both strands of DNA causing a double strand break. The double stranded break can be repaired by non-homologous end joining DNA repair, or by a homology directed repair pathway, which will result in either insertions or deletions at the break site, or by using a repair template to introduce mutations, respectively. Double-stranded breaks can also be introduced into the PSIP1 gene by expressing Transcription activator-like effector nucleases (TALENs) in the cells. TALENs are artificial restriction enzymes generated by fusing a TAL effector DNA binding domain to a DNA cleavage domain and are known in the art and can be adapted for use in embodiments of this disclosure. In yet another approach, zinc-finger nucleases (ZFNs) can be expressed in the cells to target the PSIP1 gene. ZFNs are artificial restriction enzymes produced by fusing a zinc finger DNA-binding domain to a DNA-cleavage domain. ZF domains can be designed to target PSIP1 gene DNA sequences where the zinc-finger nucleases cleave the sequence, thereby disrupting the gene. In another embodiment, site-specific gene integration or targeted integration of a sequence into specific integration sites within the gene can be accomplished by using commercial systems such as Jump-In™ or Flp-In™ systems commercially available from Thermo Fisher Scientific Inc. Multiple integration sites may be targeted by PhiC31 in the Jump-In™ Fast system. As will be recognized by those skilled in the art, a FRT site (34 bp) in the target genome is needed for gene integration, and is provided by specific commercial cell lines derived from Flp-In™ technology.

In a non-limiting reduction to practice, we used a CRISPR-CAS-9 system to design specific constructs with guide RNA (gRNA) and a complimentary region upstream of Protospacer Adjacent Motif (PAM) sequences to create double strand breaks in the target PSIP1 gene. We then selected colonies with homozygous disruption of the PSIP1 gene at the break site. A cell line such as HEp2 may have multiple copies of PSIP1 gene and it is thus important to isolate a clone where all copies of the PSIP1 gene have been disrupted, thereby eliminating the LEDGF protein from cells. Five CRISPR-CAS9 examples for PSIP1 gene disruption are described below. There are numerous PAM sites spanning across the exons and introns of the PSIP1 gene, but exons are preferred targets for CRISPR-CAS9 induced mutations or disruptions in the coding region.

Each representative sequence below includes U6 promoter sequence, gRNA targeting site and a gRNA scaffold upstream of PAM sequence which in combination with a CAS9 enzyme supplied to the cell either as part of the same vector or a different vector will create a functional CRISPR complex capable of creating a double stranded break in the targeted area of the genome.

Example Sequence 1:

(SEQ ID NO: 12):
5'GTACAAAAAAGCAGGCTTTAAAGGAACCAATTCAGTCGACTGGATCCG

GTACCAAGGTCGGGCAGGAAGAGGGCCTATTTCCCATGATTCCTTCATAT

TTGCATATACGATACAAGGCTGTTAGAGAGATAATTAGAATTAATTTGAC

TGTAAACACAAAGATATTAGTACAAAATACGTGACGTAGAAAGTAATAAT

TTCTTGGGTAGTTTGCAGTTTTAAAATTATGTTTTAAAATGGACTATCAT

ATGCTTACCGTAACTTGAAAGTATTTCGATTTCTTGGCTTTATATATCTT

GTGGAAAGGACGAAACACCGTAATCAGCCACAACATAACGTTTTAGAGCT

-continued
AGAAATAGCAAGTTAAAATAAGGCTAGTCCGTTATCAACTTGAAAAAGTG

GCACCGAGTCGGTGCTTTTTTTCTAGACCCAGCTTTCTTGTACAAAGTTG

GCATTA 3'

Example Sequence 2:

(SEQ ID NO: 13):
5'TGTACAAAAAAGCAGGCTTTAAAGGAACCAATTCAGTCGACTGGATCC

GGTACCAAGGTCGGGCAGGAAGAGGGCCTATTTCCCATGATTCCTTCATA

TTTGCATATACGATACAAGGCTGTTAGAGAGATAATTAGAATTAATTTGA

CTGTAAACACAAAGATATTAGTACAAAATACGTGACGTAGAAAGTAATAA

TTTCTTGGGTAGTTTGCAGTTTTAAAATTATGTTTTAAAATGGACTATCA

TATGCTTACCGTAACTTGAAAGTATTTCGATTTCTTGGCTTTATATATCT

TGTGGAAAGGACGAAACACCGACGCCTCTGCGGCAGCTGGGTTTTAGAGC

TAGAAATAGCAAGTTAAAATAAGGCTAGTCCGTTATCAACTTGAAAAAGT

GGCACCGAGTCGGTGCTTTTTTTCTAGACCCAGCTTTCTTGTACAAAGTT

GGCATTA 3'

Example Sequence 3:

(SEQ ID NO: 14)
5'TGTACAAAAAAGCAGGCTTTAAAGGAACCAATTCAGTCGACTGGATCC

GGTACCAAGGTCGGGCAGGAAGAGGGCCTATTTCCCATGATTCCTTCATA

TTTGCATATACGATACAAGGCTGTTAGAGAGATAATTAGAATTAATTTGA

CTGTAAACACAAAGATATTAGTACAAAATACGTGACGTAGAAAGTAATAA

TTTCTTGGGTAGTTTGCAGTTTTAAAATTATGTTTTAAAATGGACTATCA

TATGCTTACCGTAACTTGAAAGTATTTCGATTTCTTGGCTTTATATATCT

TGTGGAAAGGACGAAACACCGAGGTAGACGAAGTTCCTGAGTTTTAGAGC

TAGAAATAGCAAGTTAAAATAAGGCTAGTCCGTTATCAACTTGAAAAAGT

GGCACCGAGTCGGTGCTTTTTTTCTAGACCCAGCTTTCTTGTACAAAGTT

GGCATTA 3'

Example Sequence 4 (SEQ ID NO:15):

5'TGTACAAAAAAGCAGGCTTTAAAGGAACCAATTCAGTCGACTGGATCC

GGTACCAAGGTCGGGCAGGAAGAGGGCCTATTTCCCATGATTCCTTCATA

TTTGCATATACGATACAAGGCTGTTAGAGAGATAATTAGAATTAATTTGA

CTGTAAACACAAAGATATTAGTACAAAATACGTGACGTAGAAAGTAATAA

TTTCTTGGGTAGTTTGCAGTTTTAAAATTATGTTTTAAAATGGACTATCA

TATGCTTACCGTAACTTGAAAGTATTTCGATTTCTTGGCTTTATATATCT

TGTGGAAAGGACGAAACACCGAACTACCCATTTTCTTTTTGTTTTAGAGC

TAGAAATAGCAAGTTAAAATAAGGCTAGTCCGTTATCAACTTGAAAAAGT

GGCACCGAGTCGGTGCTTTTTTTCTAGACCCAGCTTTCTTGTACAAAGTT

GGCATTA3'

Example Sequence 5:

(SEQ ID NO: 16)
```
5'TGTACAAAAAAGCAGGCTTTAAAGGAACCAATTCAGTCGACTGGATCC
GGTACCAAGGTCGGGCAGGAAGAGGGCCTATTTCCCATGATTCCTTCATA
TTTGCATATACGATACAAGGCTGTTAGAGAGATAATTAGAATTAATTTGA
CTGTAAACACAAAGATATTAGTACAAAATACGTGACGTAGAAAGTAATAA
TTTCTTGGGTAGTTTGCAGTTTTAAAATTATGTTTTAAAATGGACTATCA
TATGCTTACCGTAACTTGAAAGTATTTCGATTTCTTGGCTTTATATATCT
TGTGGAAAGGACGAAACACCGAGTGCTTTTTTAGGACCAAGTTTTAGAGC
TAGAAATAGCAAGTTAAAATAAGGCTAGTCCGTTATCAACTTGAAAAAGT
GGCACCGAGTCGGTGCTTTTTTTCTAGACCCAGCTTTCTTGTACAAAGTT
GGCATTA 3'
```

For Example Sequence 3, the disruption was targeted into the exon 1 of the PSIP1 gene, thereby eliminating of the potential to make a partial LEDGF protein. Further, we isolated a single colony of HEp2 cells where all copies of PSIP1 gene were disrupted as confirmed by DNA sequencing. Following confirmation by DNA sequencing, the cells from the colony were mixed with WT cells in 1:1 ratio and IIF analysis was performed using a panel of anti-sera that were specifically positive for DFS70 pattern and confirmed by LIA (Line Immunoassay) or Line blot assay for DFS70 antisera (ImmcoStripe ANA-Advanced LIA, Immco Diagnostics Inc., Buffalo, N.Y.). The results are depicted in FIG. 1. Thus, the disclosure includes mammalian cell cultures which comprise mammalian cells wherein every copy of the PSIP1 gene in the cells is disrupted, and thus the cells do not express LEDGF protein. In an embodiment, the cells do not express detectable LEDGF protein, wherein the detection is by IIF. In embodiments, when the PSIP1 gene is disrupted using a CRISPR approach, the cells can further comprise a Cas9 protein coding region integrated into one or more locations in the chromosome(s) of the cells, and can further comprise a sequence encoding the gRNA integrated in the chromosome(s) of the cells.

In another aspect the disclosure includes a method for detecting ANA antibodies, and/or LEDGF antibodies. The method comprises obtaining a biological sample from an individual, mixing the sample with modified cells described herein, and performing an immno-assay, such as an IIF assay to determine the antibodies. The presence of the antibodies is a diagnosis or aids in the diagnosis of an autoimmune disease, such as SARDS, and the absence of the ANA antibodies indicate the lack of an autoimmune disease. Thus, the disclosure provides diagnostic methods using novel agents in the steps of the method. In embodiments, the presence of antibodies to LEDGF in LEDGF+ cells, is indicative that further diagnostic testing of the individual is warranted.

As noted above, IIF assays using HEp-2 cells as a substrate to detect ANA antibodies are well known in the art and can be used with the modified cells of the present disclosure without modifying such well known protocols. The biological sample that is used in the assay can be any biological sample, including but not limited to blood, serum, semen, pleural fluid, cerebrospinal fluid, saliva, urine, exosomes, or tissue. The biological sample can be used directly, or it can be subjected to a processing step before being exposed to the cells. The amount of antibodies, if any, can be compared to any suitable reference for, for instance, correcting for background, or for staging the degree and/or severity of an autoimmune disease that is positively correlated with the antibodies. In embodiments, the disclosure includes testing combinations of LEDGF+ and LEDGF− cells to determine whether or not a sample comprises antibodies that bind to LEDGF, and thus can provide for correction of background that complicates previously available approaches which frequently result in false positive results for ANA autoantibodies.

In another aspect, the disclosure includes kits and articles of manufacture for use in detecting ANA antibodies. The kit can comprise at least one container in which the modified cells of this disclosure are kept. The cells can be preserved using any suitable reagents, and can be provided, for example, in the form of a pellet. The kit can include reagents for use in IIF assays, and instruction which describe the modified cells, such as by providing a description of how or that they have been modified to reduce DFS, and instructions for using the cells in the IIF assays. In embodiments, the kits comprise LEDGF+ and LEDGF− cells which are fixed to one or more suitable solid substrates. The cells may be permeabilized using any suitable approach, many of which are well known in the art, and are thus killed cells. In embodiments, the fixed cells that are immobilized on the solid substrate are dried.

It will be apparent form the foregoing that the present disclosure includes the modified cells described herein, the methods for making the modified cells, cell cultures comprising the modified cells, and all methods for using the modified cells in any assay designed to detect any one, or any combination of the antibodies that are comprised by the ANA antibody profile.

REFERENCES

Ayaki, M., T. Sueno, D. P. Singh, L. T. Chylack, Jr. and T. Shinohara (1999). "Antibodies to lens epithelium-derived growth factor (LEDGF) kill epithelial cells of whole lenses in organ culture." Exp Eye Res 69(1): 139-142.

Ganapathy, V. and C. A. Casiano (2004). "Autoimmunity to the nuclear autoantigen DFS70 (LEDGF): what exactly are the autoantibodies trying to tell us?" Arthritis Rheum 50(3): 684-688.

Ganapathy, V., T. Daniels and C. A. Casiano (2003). "LEDGF/p75: a novel nuclear autoantigen at the crossroads of cell survival and apoptosis." Autoimmun Rev 2(5): 290-297.

Mahler, M. and M. J. Fritzler (2012). "The Clinical Significance of the Dense Fine Speckled Immunofluorescence Pattern on HEp-2 Cells for the Diagnosis of Systemic Autoimmune Diseases." Clin Dev Immunol 2012: 494356.

Mahler, M., T. Parker, C. L. Peebles, L. E. Andrade, A. Swart, Y. Carbone, D. J.

Ferguson, D. Villalta, N. Bizzaro, J. G. Hanly and M. J. Fritzler (2012). "Anti-DFS70/LEDGF Antibodies Are More Prevalent in Healthy Individuals Compared to Patients with Systemic Autoimmune Rheumatic Diseases." J Rheumatol.

Ochs, R. L., Y. Muro, Y. Si, H. Ge, E. K. Chan and E. M. Tan (2000). "Autoantibodies to DFS 70 kd/transcription coactivator p75 in atopic dermatitis and other conditions." J Allergy Clin Immunol 105(6 Pt 1): 1211-1220.

Ogawa, Y., K. Sugiura, A. Watanabe, M. Kunimatsu, M. Mishima, Y. Tomita and Y. Muro (2004). "Autoantigenicity of DFS70 is restricted to the conformational epitope of C-terminal alpha-helical domain." J Autoimmun 23(3): 221-231.

Okamoto, M., Y. Ogawa, A. Watanabe, K. Sugiura, Y. Shimomura, N. Aoki, T. Nagasaka, Y. Tomita and Y. Muro (2004). "Autoantibodies to DFS70/LEDGF are increased in alopecia areata patients." *J Autoimmun* 23(3): 257-266.

Vandekerckhove, L., F. Christ, B. Van Maele, J. De Rijck, R. Gijsbers, C. Van den Haute, M. Witvrouw and Z. Debyser (2006). "Transient and stable knockdown of the integrase cofactor LEDGF/p75 reveals its role in the replication cycle of human immunodeficiency virus." *J Virol* 80(4): 1886-1896.

Watanabe, A., M. Kodera, K. Sugiura, T. Usuda, E. M. Tan, Y. Takasaki, Y. Tomita and Y. Muro (2004). "Anti-DFS70 antibodies in 597 healthy hospital workers." *Arthritis Rheum* 50(3): 892-900.

While the disclosure has been particularly shown and described with reference to specific embodiments, it should be understood by those having skill in the art that various changes in form and detail may be made therein without departing from the spirit and scope of the present disclosure as disclosed herein.

What is claimed is:

1. An in vitro composition comprising Hep-2 cells immobilized on a solid substrate, comprising: Hep-2 cells comprising a modification genomic DNA that reduces the expression of lens epithelium derived growth factor (LEDGF) protein; and
    non-genomically modified Hep-2 cells comprising the LEDGF protein, wherein the composition comprises from about 50% to about 95% genomically modified cells.

2. The in vitro composition of claim 1, wherein the Hep-2 cells are killed and permeabilized.

3. The in vitro composition of claim 1, wherein said LEDGF protein is present in a complex with a primary antibody which binds to LEDGF protein.

4. The in vitro composition of claim 3, wherein the genomically modified Hep-2 cells comprise a chromosome comprising the nucleic acid sequence of SEQ ID NO: 14.

5. The in vitro composition of claim 1, wherein the composition comprises about 85% to about 95% genomically modified cells.

6. The in vitro composition of claim 1, wherein the modification to genomic DNA comprises a gene encoding a detectable protein which has replaced the gene encoding the LEDGF protein (PSIP1 gene).

7. The in vitro composition of claim 1, further comprising:
    auto-antigens to which anti-nuclear autoantibodies bind; and
    anti-human secondary antibodies that bind to the anti-nuclear autoantibodies.

8. The in vitro composition of claim 1, wherein the genomically modified Hep-2 cells do not express a detectable amount of LEDGF.

* * * * *